Dec. 25, 1962 J. G. STROPKEY Plant Pat. 2,204
LILAC BUSH
Filed Jan. 3, 1961 2 Sheets-Sheet 1
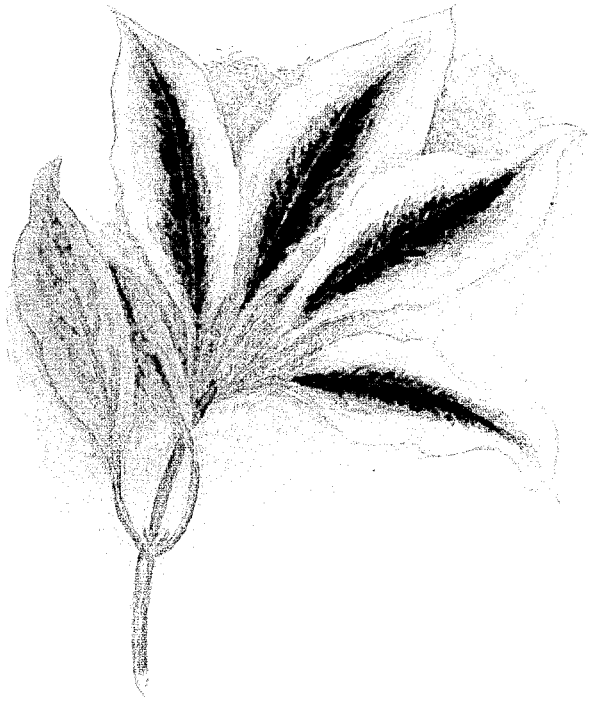
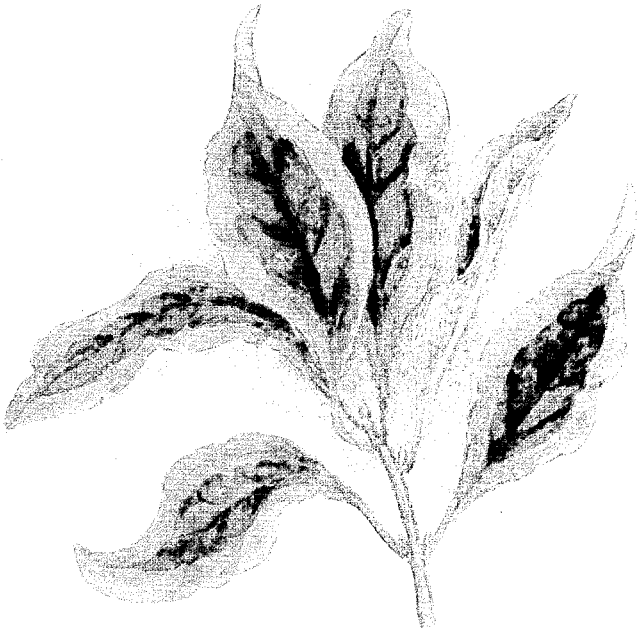
WITNESS
Addison E. Avery
INVENTOR
JOHN G. STROPKEY
by Rummler & Snow
ATTYS.

Dec. 25, 1962 J. G. STROPKEY Plant Pat. 2,204
LILAC BUSH
Filed Jan. 3, 1961 2 Sheets-Sheet 2
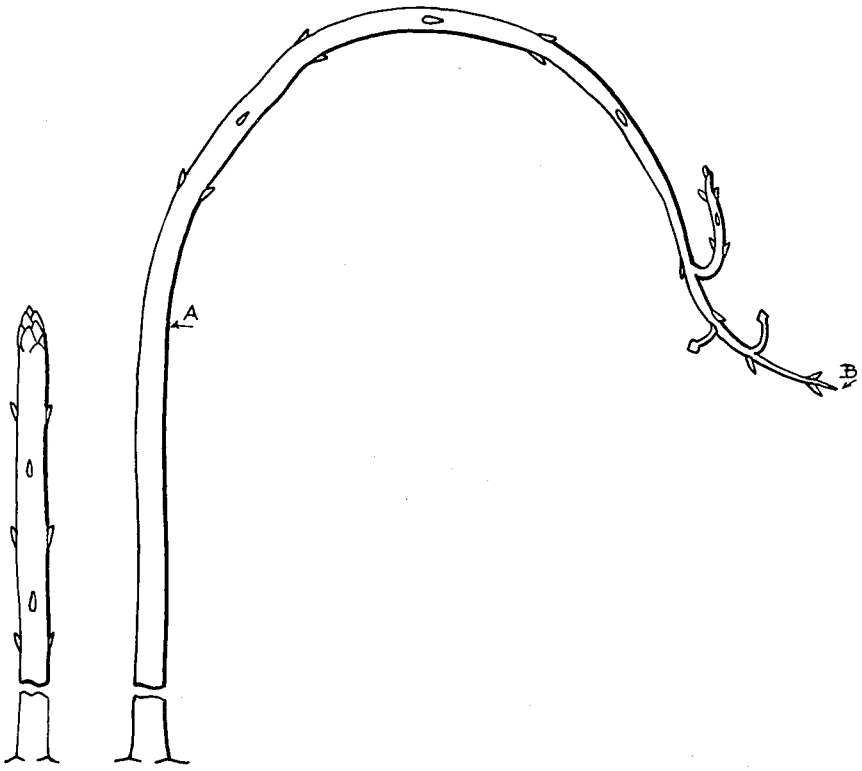
INVENTOR:
JOHN G. STROPKEY
BY Kenmuler & Snow
ATT'YS United States Patent Office Plant Pat. 2,204
Patented Dec. 25, 1962

2,204
LILAC BUSH

John G. Stropkey, 485 Bowhall Road, Painesville, Ohio
Filed Jan. 3, 1961, Ser. No. 80,509
1 Claim. (Cl. 47—60)

This invention relates to a new and distinct variety of *Syringa josikaea* plant which occurred as a seedling resulting from a cross, made at my nurseries at Painesville, Ohio, between an unknown pollen parent and a seed parent of a conventional, unpatented, *josikaea* variety.

My new variety is the result of breeding efforts carried on by me and my associates for many years at Painesville, Ohio, with the objective of producing a lilac plant having a more attractive appearance after blooming and which would retain its attractiveness throughout the period that its foliage would remain on the plant. Because of their attractiveness while in bloom, lilac plants have enjoyed a long popularity. However, after blooming their decorative characteristic is gone and all that remains is a rather ordinary leafy bush. For that reason I have sought to produce a lilac plant which would have a distinctive and decorative foliage and which would retain its attractiveness long after the blooms had disappeared and until the foliage dried. This objective, I believe, has been accomplished in the new variety herein disclosed, which was discovered by me at my nursery in 1954.

My new variety is distinguished by its variegated foliage, the leaves of a two-year and older plant having a green central portion which fades marginally into a yellow color and then to an undulating creamy green or white border at the leaf margins. During the first year of growth, after bud grafting, the leaves of my new variety do not have a pronounced variegation as above described, but rather ahve a medium green central portion and light green margins. During the second year, however, and as the plant grows older, the variegation from green to yellow and white becomes sharply apparent and from then on the foliage retains its distinctive appearance and provides an attractive, decorative bush throughout the summer and until the foliage dries, the variegated leaves giving a flashing, constantly changing reflection, in light and shadow, as the leaves are rustled by the wind.

I have asexually reproduced my new variety, by bud grafting, in my nurseries at Painesville, Ohio, and its novel characteristics have been found to hold true to form in succeeding generations of the new plant.

The accompanying drawing, in full color, illustrates the novel features of the foliage of the new plant, the upper figure showing the foliage of a five-year plant wherein the lower younger leaves have a light green center portion and greenish white margins which changes to a sharper contrast of green-yellow-white as the leaves develop. The lower figure of the illustration shows the nature of the green to pale green variegation of the leaves of the one-year plant.

The second sheet of drawings, in pen and ink, shows a single shoot, partly broken away, as it grows from the root during the first two years to a height of about three to four feet; and the same shoot as the flower support bends or droops during the first blooming season, the flower support arching from A to B in one season's growth and producing a crooked branching and weeping appearance to the plant.

A more detailed specification of my new lilac variety is as follows:

*Plant*

Seedling:

*Seed parent.*—*Josikaea* (unpatented).
*Pollen parent.*—Unknown.

Classification: Syringa hybrid.
Form: Bush.
Height: 4 to 5 feet, after two years of growth.
Growth: Vigorous, fast growing young shoots during first two years, slow growing thereafter. Branching during second year. Sturdy and upright until beginning to bloom and then bloom canes bend or droop over and thus appear to weep.
Foliage: Abundant.
*Size of leaf.*—Varying—2 to 6 inches in length.
*Shape.*—Lanceolate and oblong, cuspidate tip—and wavy margins.
*Texture.*—Smooth. Glossy when young.
*Color.*—Older leaf: upper side—green center bordered with yellow, cream colored margins; underside—same as upper side, but with less pronounced contrast and of a lighter, greyish cast. Young leaves: upper side—green central portion with light green margins; under side—similar to upper side but with a greyish cast.
*Petioles.*—Length; about one-half inch.
*Ribs and veins.*—Smooth, protruding from underside surface of leaf.
*Rachis.*—Smooth and strong. Plainly protruding.

*Bud*

Size: Very much like *josikaea.*
Form: Ovoid and pointed. Opens slowly.
Color: When sepals first divide; light green. When sepals begin to unfurl; pink.
Sepals: Branched, upstanding and curling back. Spear-shaped. Color: inside—whitish pink; outside—pink.
Calyx: Funnel-shaped. Does not split and has smooth, glandular aspect.
Peduncle: Length; approximately one-fourth to one-half inch. Erect and of green color.

*Flower*

Blooms: Profusely. Once in late spring.
Borne: Singly.
Size: Average size, full floret clusters approximately 4 to 6 inches in length.
Shape: Same as *josikaea*; flat form when bloom first opens. Changing later to a cluster of more pointed form.
Petalage: Same form as *josikaea* with clustered florets each having 3 or 4 petals, some florets with two petals. Petals stay on stem until dry and go to seed.
Color: Outer petal—pink; base—greenish white. Inside petal—dainty, orchid pink tint over entire surface. Reverse side—orchid.
Peduncle: Length, one-half inch before terminal; sturdy and upright. Color, forest green.
Discoloration: Turns to lilac pink after full bloom.
Texture: Soft.
Fragrance: Very pronounced—typical lilac fragrance.
Persistence: Not affected by wet or hot weather, tends to hang on and dry.
Insect resistance: Good. Resistant to scale and borers, as tested and observed in my nurseries at Painesville, Ohio, where such insects are present on other lilac varieties grown in the immediate area.
Lasting quality: On plant—good. As cut flower—very good.
Genital organs: Same as *josikaea.* However, ovaries seem to be weaker than *josikaea.*
Fruit: Same as *josikaea.* Oblong shape, brown color at maturity, and about ten percent fertile.

The color of the variegated leaves of the new plant, according to "A Dictionary of Color," by Maerz and Paul, are as follows:

UPPER FIGURE

| | Plate | Letter | Number |
|---|---|---|---|
| Top of leaf: | | | |
| Outer margin—creamy greenish white | 9 | B | 1 |
| Inner border—yellow | 9 | L | 1 |
| Center portion—green | 18 | L | 6 |
| to green | 20 | L | 8 |
| Under side of leaf—margin—grey green | 19 | D | 2 |

LOWER FIGURE

| | | | |
|---|---|---|---|
| Top side of leaf: | | | |
| Outer margin—green | 18 | L | 5 |
| Center portion—green | 20 | L | 6 |
| to green | 20 | L | 8 |
| Underside of leaf—grey green | 19 | D | 2 |

My new variety of lilac most nearly resembles *Syringa josikaea,* as far as the flowers are concerned. However, at first glance or casual observance the plant, in some forms, looks to be like *Wiegela nana* Variegated and in other forms somewhat like *Cornus florida* Variegated.

The new variety, however, is particularly distinguished by its very different, rather crooked, branching, which results from the drooping or weeping of its bloom canes; and the distinctive coloring of its leaves. The new variety is a slower growing plant, after the first few years, and for that reason is an excellent one for modern landscaping of ranch type homes. Its distinctively variegated leaves also provide a pleasing decorative effect lasting throughout the entire spring and summer seasons.

Having thus described my new variety of lilac plant I claim:

A new and distinct variety of Syringa plant, substantially as herein shown and described, characterized particularly by its variegated foliage which during the second year of growth, acquires a distinct yellow inner border surrounding a green central leaf area and a cream colored outer margin bordering the entire leaf; the plant being further characterized by its more crooked branching and its slower growth after attaining a height of about five feet, by the weeping effect of its bloom canes after the flowers are in full bloom, by its very fragrant flowers which are of a dainty pink color when first opened, and which turn to a somewhat darker lilac pink as the bloom ages; and by the fact that the foliage retains its distinctive variegation throughout the entire growing season.

No references cited.